(12) United States Patent
Molina et al.

(10) Patent No.: US 7,199,230 B2
(45) Date of Patent: Apr. 3, 2007

(54) NUCLEIC ACIDS ENCODING DURAMYCIN

(75) Inventors: Luis Molina, Durham, NC (US);
Charles J. Romeo, Carrboro, NC (US)

(73) Assignee: Molichem Medicines, Inc., Chapel Hill, NC (US)

( * ) Notice: Subject to any disclaimer, the term of this patent is extended or adjusted under 35 U.S.C. 154(b) by 157 days.

(21) Appl. No.: 10/530,584

(22) PCT Filed: Sep. 22, 2003

(86) PCT No.: PCT/US03/29852

§ 371 (c)(1),
(2), (4) Date: Apr. 7, 2005

(87) PCT Pub. No.: WO2004/033706

PCT Pub. Date: Apr. 22, 2004

(65) Prior Publication Data

US 2006/0141564 A1    Jun. 29, 2006

(51) Int. Cl.
*C07H 21/00* (2006.01)
*C12N 1/00* (2006.01)
(52) U.S. Cl. ............... 536/23.4; 536/23.1; 435/243
(58) Field of Classification Search ............ None
See application file for complete search history.

(56) References Cited

U.S. PATENT DOCUMENTS 6,342,385 B1 * 1/2002 Qi et al. ............... 435/252.3
2004/0101963 A1 * 5/2004 Bibb et al. ............... 435/455

\* cited by examiner

*Primary Examiner*—Robert A. Wax
(74) *Attorney, Agent, or Firm*—King & Spalding LLP

(57) ABSTRACT

Nucleic acids encoding preduramycin and produramycin are described, along with recombinant nucleic acids and host cells containing the same and methods of use thereof, such as for the manufacture of the lantibiotic duramycin.

14 Claims, 2 Drawing Sheets

| | |
|---|---|
| CKQSCSFGPFTFVCDGNTK | DURAMYCIN (SEQ ID NO:5) |
| CRQSCSFGPFTFVCDGNTK | CINNAMYCIN (SEQ ID NO:8) |
| CRQSCSFGPLTFVCDGNTK | DURAMYCIN B (SEQ ID NO:9) |
| CANSCSYGPLTWSCDGNTK | DURAMYCIN C (SEQ ID NO:10) |
| CVQSCSFGPLTWSCDGNTK | ANCOVENIN (SEQ ID NO:11) |

```
         MOL3 (SEQ ID NO:16)
CCTCAACATCGGAGGTAAGCCATGACCGCTTCCATTCTTCAGCAGTCCGT   50
MOL1 (SEQ ID NO:14)                MOL5 (SEQ ID NO:18)

CGTGGACGCCGACTTCCGCGCGGCGCTGCTTGAGAACCCCGCCGCCTTCG  100

GCGCTTCCGCCGCGGCCCTGCCCACGCCCGTCGAGGCCCAGGACCAGGCG  150

TCCCTTGACTTCTGGACCAAGGACATCGCCGCCACGGAAGCCTTCGCCTG  200

CCGCCAGAGCTGCAGCTTCGGCCCGTTCACCTTCGTGTGCGACGGCAACA  250
                                MOL6 (SEQ ID NO:19)
    MOL4 (SEQ ID NO:17)
CCAAGTAAGTGGCTGCTGCCTCTAGGCGGTAATGC  285 (SEQ ID NO:12)
        MOL2 (SEQ ID NO:15)
```

FIG. 3

DURAMYCIN    MTASILQ-SVVDADFRAALIENPAAFGASTAVLP
CINNAMYCIN   MTASILQQSVVDADFRAALLENPAAFGASAAALP
                    *           *        * *

DURAMYCIN    TPVEQQDQASLDFWTKDIAATEAFACKQSCSFGP
CINNAMYCIN   TPVEAQDQASLDFWTKDIAATEAFACRQSCSFGP
                *                        *

DURAMYCIN    FTFVCDGNTK (SEQ ID NO:3)
CINNAMYCIN   FTFVCDGNTK (SEQ ID NO:13)

FIG. 4

NUCLEIC ACIDS ENCODING DURAMYCIN

FIELD OF THE INVENTION

The invention relates to nucleic acids sequences encoding the peptide lantibiotic duramycin.

BACKGROUND OF THE INVENTION

Lantibiotics are bactericidal peptides that contain the rare amino acids lanthionine and/or 3-methyllanthionine. Lantibiotics are produced by gram-positive bacteria and are derived from ribosomally-synthesized prepeptides. The prepeptides typically consist of an N-terminal leader sequence, which is cleaved off during or after secretion from the cell, and the C-terminal propeptide, which is post-translationally modified to form the mature lantibiotic (Jung (1991) Angewandte Chemie 30(9):1051–1192). One such post-translational modification comprises the enzymatic dehydration of serine or threonine residues to yield dehydroalanine (Dha) or dehydrobutyrine (Dhb), respectively (Weil, et al. (1990) Eur. J. Biochem. 194:217–223). Subsequently, SH-groups of the cysteine residues react with the double-bonds of Dha or Dhb residues to form lanthionine or methyllanthionine, respectively.

Lantibiotics are structurally and functionally diverse molecules. They range from elongated, cationic peptides of 34 amino acid residues in length to short, 19 amino acid, globular molecules with a net negative charge. Based on their structural and functional properties, the mature peptides have been subdivided into two groups, Type-A and Type-B (Jung (1991) supra). Type-A lantibiotics are elongated amphiphilic peptides that form transient pores in the membranes of sensitive bacteria (Sahl (1991) In G. Jung and H.-G. Sahl (ed.), Nisin and novel lantibiotics (p. 347–358) Escom, Leiden). Type-B lantibiotics are globular peptides produced by Streptomyces. They have molecular masses less than 2100 Da, share a high degree of amino acid sequence homology and have similar ring structures comprised of a head-to-tail condensation (Jung (1991), supra).

The Type-A class has been further divided into subgroups according to their propeptide sequences (Sahl and Bierbaum (1998) Annu. Rev. Microbiol. 52:41–79). Subgroup AI contains the nisin-like lantibiotics such as nisin, subtilin, epidermin and pep5 as the most thoroughly characterized members (Allgaier, et al. (1986) Eur. J. Biochem. 160:9–22; Gross, et al. (1968) FEBS Lett 2:61–64; Gross, et al. (1971) J Am. Chem. Soc. 93:4634–4635; Kaletta, et al. (1989) Arch. Microbiol. 152:16–19; Weil, et al. (1990) Eur. J. Biochem. 194:217–223). Subgroup AII consists of lacticin 481, SA-FF22, salivaricin and variacin (Hynes, et al. (1993) Appl. Environ. Microbiol. 59:1969–1971; Piard, et al. (1993) J. Biol. Chem. 268:16361–16368; Pridmore, et al. (1996) Appl. Environ, Microbiol. 62:1799–1802; Ross, et al. (1993) Appl. Environ. Microbiol. 59:2014–2021).

Another characteristic feature of lantibiotics is the prepeptide leader sequence, which is unrelated to the more common signal sequences utilized in sec-dependent transport systems. The leader peptides may play an important role in maturation of the lantibiotic through interactions with the modifying enzymes and transport system as well as the propeptide. Therefore, individual specificities may exist between the components of the modification system and the corresponding prepeptides upon which they operate. Grouping and classifying lantibiotics based on the leader peptide sequence is consistent with the classifications describe above (Sahl and Bierbaum (1998) supra).

The genes responsible for the biosynthesis of the lantibiotics are organized in operon-like structures. The biosynthetic locus of all members in subgroup AI comprises lanA, the structural gene for the lantibiotic; lanB and lanC, which encode the post-translational modifying enzymes of the preprolantibiotic; lanP, which encodes the processing protease; and lanT, which encodes the ABC transporter for secretion of the lantibiotic. Epidermin and gallidermin have an additional gene, lanD, which is responsible for C-terminal oxidative decarboxylation (Kupke, et al. (1994) J. Biol. Chem. 269:5653–5659; Kupke, et al. (1995) J. Biol. Chem. 270:11282–89).

In comparison, subgroup AII lantibiotics have simple biosynthetic loci. They are comprised of lanB and lanC, which are combined into one gene; lanM; and lanP and lanT, which are combined into lanT. (Chen, et al. (1999) Appl. Environ. Microbiol. 65:1356–1360; Qi, et al. (1999) Appl. Environ. Microbiol 65:652–658; Rince, et al. (1994) Appl. Environ. Microbiol. 60:1652–1657). Lantibiotic loci also contain a set of immunity genes, which are responsible for self-protection of the producing strains (Saris, et al. (1996) Antonie van Leeuwenhoek 69:151–159). Moreover, the expression of the lantibiotic genes is usually regulated either by a single transcriptional regulator (Peschel, et al. (1993) Mol. Microbiol. 9:31–39; Qi, et al. (1999) supra) or by a two-component signal transduction system (de Ruyter, et al. (1996) J. Bacteriol. 178:3434–3439; Klein, et al. (1993) Appl. Environ Microbiol. 59:296–303; Kuipers, et al. (1995) J. Biol. Chem. 270:27295–27304).

The lantibiotic duramycin, also known as PA48009 (FIG. 1), was isolated from the culture supernatant of Streptoverticillium cinnamoneum forma azacoluta (ATCC 12686; now referred to as Streptomyces cinnamoneus subsp. cinnamoneus) (Hayashi, et al., (1990) J. Antibiotics 43:1421; Pridham, et al. (1956) Phytopathology 46:575–581; Shotwell, et al. (1958) J. Am. Chem. Soc. 80:3912; Nakamura, et al. (1984) Biochem. 23:385). Duramycin contains a lysinoalanine, head-to-tail cross-bridge and a hydroxylated aspartic acid. Lysinoalanine results from an analogous reaction of the epsilon-$NH_2$ group of lysine with dehydrolalanine. The ability of duramycin to increase chloride secretion has been reported (Stone, et al. (1984) J. Biol. Chem. 259: 2701; Cloutier, et al. (1987) Pediatr. Pulmonol. 1(Suppl): 112; Cloutier, et al. (1988) Pediatr. Pulmonol. 2(Suppl):99; Cloutier, et al. (1989) Pediatr. Pulmonol. 4(Suppl):116; Cloutier, et al. (1990) Am. J. Physiol. 259:C450). The use of duramycin for facilitating the removal of retained pulmonary mucus secretions has been provided (e.g., U.S. Pat. Nos. 5,849,706 and 5,716,931). Furthermore, duramycin inhibits the growth of B. subtilis by binding to phosphatidylethanolamine.

SUMMARY OF THE INVENTION

The present invention provides a genetic locus of Streptomyces cinnamoneus subsp. cinnamoneus which encodes for duramycin. Examples of the gene and peptides encoded by the gene are also provided.

An object of the present invention is to provide a nucleic acid sequences isolated from S. cinnamoneus which encode for duramycin or fragments thereof. The nucleic acid sequences referred to herein are those which encode for preduramycin (SEQ ID NO:2), produramycin (SEQ ID NO:4), the preduramycin leader sequence (SEQ ID NO:6), or fragments thereof.

Stated otherwise, the present invention provides an isolated nucleic acid selected from the group consisting of: (a)

a nucleic acid according to SEQ ID NO: 2 encoding preduramycin; (b) a nucleic acid according to SEQ ID NO: 4 encoding produramycin; (c) nucleic acids that are at least 90, 95 or even 99 percent identical in sequence to nucleic acids of (a) or (b) above (or have such identiy to the preduramycin leader sequence of SEQ ID NO: 6) and which encode preduramycin or produramycin, and/or nucleic acids which hybridize to said sequences of (a) or (b) above or the complement thereof, such as under stringent hybridization conditions, and encode preduramycin or produramycin; and (d) nucleic acids that differ from the nucleic acids of (a), (b), or (c) above due to the degeneracy of the genetic code, and which encode a preduramycin or produramycin encoded by a nucleic acid of (a), (b), or (c) above.

Another object of the present invention is to provide peptides encoded by the duramycin gene and vectors and host cells comprising nucleic acid sequences encoding these peptides. The peptide sequences referred to herein are preduramycin (SEQ ID NO:3), produramycin (SEQ ID NO:5), the preduramycin leader (SEQ ID NO:7) and derivatives thereof.

Another object of the invention is to provide an expression vector containing at least a fragment of any of the claimed nucleotide sequences and host cells comprising this vector. The invention further provides the expression of a peptide or fragment thereof encoded by a nucleotide as given above (e.g., the peptide provided herein as SEQ ID NO: 5). Such peptides may be isolated and/or purified in accordance with known techniques.

Another object of the invention is to provide a method for producing the preduramycin, produramycin or mature duramycin peptides. The method comprises introducing into a suitable host cell a nucleic acid sequence encoding preduramycin or produramycin, culturing said cell under suitable conditions to produce such peptides, and isolating preduramycin, produramycin or mature duramycin produced by said cell. Preferably the host cell is a gram-positive bacterium, such as from the genus *Bacillus, Streptomyces* or *Streptococcus*.

A further object of the invention is to provide a method of producing recombinant lantiobiotics by fusing the preduramycin leader sequence to other known lantibiotic sequences through genetic engineering.

The foregoing and other objects and aspects of the present invention are explained in detail in the specification set forth below.

BRIEF DESCRIPTION OF THE DRAWINGS

FIG. 3 shows the nucleic acid sequence encoding cinnamycin (GENBANK® Accession No. X58545; SEQ ID NO:12). Location of forward (Mol 1, 3, 5) and reverse (Mol 2, 4, 6) PCR primers used to amplify the duramycin structural gene are indicated.

FIG. 4 shows a prepeptide sequence comparison between duramycin (SEQ ID NO:3) and cinnamycin (SEQ ID NO:13). Propeptide sequences are underlined. *Denotes amino acid difference.

DETAILED DESCRIPTION OF PREFERRED EMBODIMENTS

Figures 1, 2:
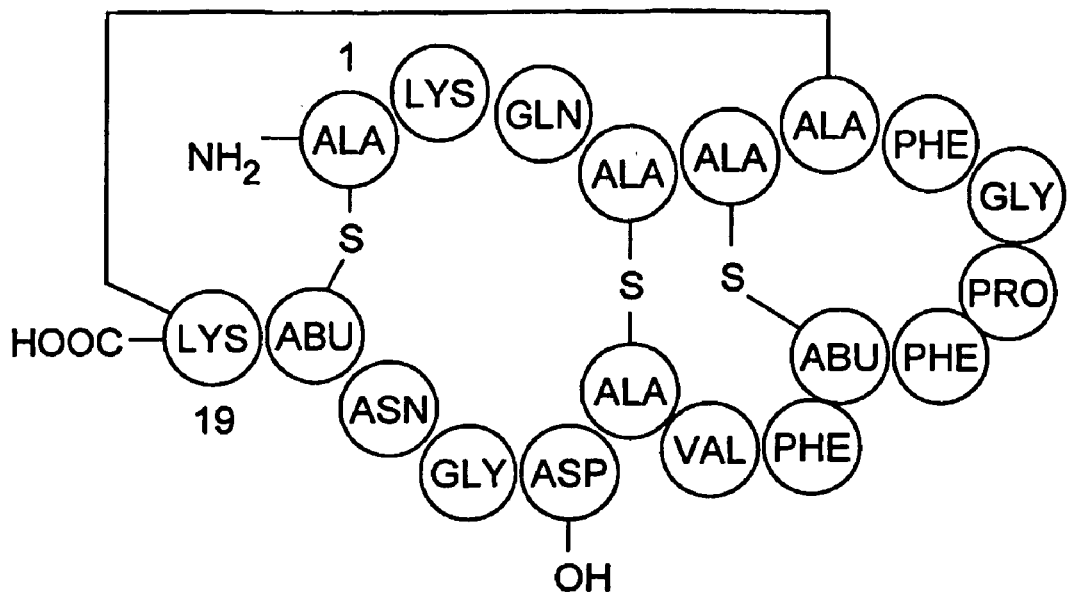
FIG. 1 depicts the structure of duramycin (modified from Sahl and Bierbaum (1998) supra).
FIG. 2 shows the propeptide amino acid sequence similarity of Type-B lantibiotics produced by *Streptomyces*.

The present invention will now be described more fully hereinafter with reference to the accompanying figures, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 C.F.R §1.822 and established usage. See, e.g., Patent In User Manual, 99–102 (November 1990) (U.S. Patent and Trademark Office).

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

The term "hybridization", as used herein, refers to any process by which a strand of nucleic acid binds with a complementary strand through base pairing. The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, *J. Org. Chem.* 35:3800 (1970); Sprinzl, et al., *Eur. J. Biochem.*, 81:579 (1977); Letsinger, et al., *Nucl. Acids Res.* 14:3487 (1986); Sawai, et al., *Chem. Lett.*, 805 (1984), Letsinger, et al., *J. Am. Chem. Soc.*, 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al, Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research," Ed. Y. S. Sanghui and P. Dan Cook; Mesmaeker, et al., Bioorganic & Medicinal Chem. Lett. 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research," Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169–176). Several nucleic acid analogs are described in Rawls, C & E News, Jun. 2, 1997, page 35. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

Nucleic acid sequences provided herein are summarized in Table 1.

TABLE 1

| TYPE | SEQUENCE | SEQ ID NO: |
|---|---|---|
| Duramycin Genomic Locus | CCTCAACATCGGAGGTAAGTCATGACCG CTTCGATTCTTCAGTCCGTCGTGGACGC CGACTTCCGCGCCGCGCTGATCGAGAAC CCGGCCGCGTTCGGTGCCTCGACCGCGG TCCTGCCCACGCCCGTGGAGCAGCAGGA CCAGGCGTCCCTCGACTTCTGGACCAAG GACATCGCCGCTACGGAAGCCTTCGCCT | SEQ ID NO: 1 |

TABLE 1-continued

| TYPE | SEQUENCE | SEQ ID NO: |
|---|---|---|
| | GCAAGCAGAGCTGCAGCTTCGGCCCGTT CACCTTCGTGTGTGACGGCAACACCAAG TAAGGCGGCCGTTGCCCTC | |
| Preduramyin Coding Sequence | ATGACCGCTTCGATTCTTCAGTCCGTCGT GGACGCCGACTTCCGCGCCGCGCTGATCG AGAACCCGGCCGCGTTCGGTGCCTCGACC GCGGTCCTGCCCACGCCCGTGGAGCAGCA GGACCAGGCGTCCCTCGACTTCTGGACCA AGGACATCGCCGCTACGGAAGCCTTCGCC TGCAAGCAGAGCTGCAGCTTCGGCCCGTT CACCTTCGTGTGTGACGGCAACACCAAG | SEQ ID NO: 2 |
| Preduramycin Amino Acid Sequence | MTASILQSVVDADFRAALIENPAAFGAST AVLPTPVEQQDQASLDFWTKDIAATEAFA CKQSCSFGPFTFVCDGNTK | SEQ ID NO: 3 |
| Produramycin Coding Sequence | TGCAAGCAGAGCTGCAGCTTCGGCCCGTT CACCTTCGTGTGTGACGGCAACACCAAG | SEQ ID NO: 4 |
| Produramycin Amino Acid Sequence | CKQSCSFGPFTFVCDGNTK | SEQ ID NO: 5 |
| Preduramycin Leader Coding Sequence | ATGACCGCTTCGATTCTTCAGTCCGTCGT GGACGCCGACTTCCGCGCCGCGCTGATCG AGAACCCGGCCGCGTTCGGTGCCTCGACC GCGGTCCTGCCCACGCCCGTGGAGCAGCA GGACCAGGCGTCCCTCGACTTCTGGACCA AGGACATCGCCGCTACGGAAGCCTTCGCC | SEQ ID NO: 6 |
| Preduramycin Leader Amino Acid Sequence | MTASILQSVVDADFRAALIENPAAFGAST AVLPTPVEQQDQASLDFWTKDIAATEAFA | SEQ ID NO: 7 |

Polynucleotides of the present invention include those coding for proteins homologous to, and having essentially the same biological properties as, the proteins disclosed herein, and particularly the DNA disclosed herein in Table 1 and encoding the compounds described in Table 1. This definition is intended to encompass natural allelic sequences thereof. Such polynucleotides are preferably of bacterial origin, particularly gram positive bacterial origin. Thus, polynucleotides that hybridize to DNA disclosed herein (or fragments or derivatives thereof which serve as hybridization probes as discussed below) and which code on expression for a product described herein are also an aspect of the invention. Conditions which will permit other polynucleotides that code on expression for a lantibiotic of the present invention to hybridize to the DNA of Table 1 or a fragment thereof can be determined in accordance with known techniques. For example, hybridization of such sequences may be carried out under conditions of reduced stringency, medium stringency or even stringent conditions (e.g., conditions represented by a wash stringency of 35–40% Formamide with 5× Denhardt's solution, 0.5% SDS and 1×SSPE at 37° C.; conditions represented by a wash stringency of 40–45% Formamide with 5× Denhardt's solution, 0.5% SDS, and 1×SSPE at 42° C.; and conditions represented by a wash stringency of 50% Formamide with 5× Denhardt's solution, 0.5% SDS and 1×SSPE at 42° C., respectively) to DNA of Table 1 in a standard hybridization assay. See, e.g., J. Sambrook et al., *Molecular Cloning, A Laboratory Manual* (2d Ed. 1989) (Cold Spring Harbor Laboratory). In general, sequences which code for proteins of the present invention and which hybridize to the DNA of Table 1 herein (or the complementary strand thereof) will be at least 75% homologous, 85% homologous, and even 95% homologous or more with those of Table 1 (the term "homologous" being used interchangeably with "sequence identity" or "identical" herein).

Further, polynucleotides that code for antibiotics of the present invention, or polynucleotides that hybridize to that as Table 1, but which differ in codon sequence from them due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

Although nucleotide sequences which encode lantibiotics of the invention are preferably capable of hybridizing to the nucleotide sequence of the naturally occurring protein or peptide of the invention under appropriately selected conditions of stringency, it may be advantageous to produce nucleotide sequences encoding the protein or peptide of the invention or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding the protein or peptide of the invention and its derivatives without altering the encoded amino acid sequences include the production of RNA transcripts having more desirable properties, such as a greater half-life, than transcripts produced from the naturally occurring sequence.

As is known in the art, a number of different programs can be used to identify whether a nucleic acid has sequence identity or similarity to a known sequence. Sequence identity and/or similarity is determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48, 443 (1970), by the search for similarity method of Pearson & Lipman, *Proc. Natl. Acad. Sci. USA* 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," *Macromolecule Sequencing and Synthesis*, Selected Methods and Applications, pp 127–149 (1988), Alan R. Liss, Inc.

An example of a useful algorithm is the BLAST algorithm, described in Altschul et al., *J. Mol. Biol.* 215, 403–410, (1990) and Karlin et al., *Proc. Nail. Acad. Sci. USA* 90, 5873–5787 (1993). A particularly useful BLAST program is the WU-BLAST-2 program which was obtained from Altschul et al., *Methods in Enzymology*, 266, 460–480 (1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

"Percent (%) nucleic acid sequence identity" with respect to the coding sequence of the polypeptides identified herein is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequences in the Figures, it is understood that in one embodiment, the percentage of sequence identity will be determined based on the number of identical amino acids in relation to the total number of amino acids. Thus, for example, sequence identity of sequences shorter than that shown in the Figure, as discussed below, will be determined using the number of amino acids in the shorter sequence, in one embodiment. In percent identity calculations relative weight is not assigned to various manifestations of sequence variation, such as, insertions, deletions, substitutions, etc.

The invention also encompasses production of DNA sequences, or fragments thereof, which encode lantibiotics of the invention entirely by synthetic chemistry. After production, the synthetic sequence may be inserted into any of the many available expression vectors and cell systems using reagents that are well known in the art. Moreover, synthetic chemistry may be used to introduce mutations into a sequence encoding the protein or peptide of the invention or any fragment thereof.

Knowledge of the nucleotide sequence as disclosed herein in Table 1, including fragments thereof (preferably at least 5, 7 or 10 nucleotides in length) can be used to generate hybridization probes which specifically bind to the DNA of the present invention or to mRNA to determine the presence of amplification or overexpression of the proteins of the present invention.

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,817,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. (Applicant specifically intends that the disclosure of all patent references cited herein be incorporated herein in their entirety by reference).

A vector is a replicable DNA construct. Vectors are used herein either to amplify DNA encoding the proteins of the present invention or to express the proteins of the present invention. An expression vector is a replicable DNA construct in which a DNA sequence encoding the proteins of the present invention is operably linked to suitable control sequences capable of effecting the expression of proteins of the present invention in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself. Expression vectors should contain a promoter and RNA binding sites that are operably linked to the gene to be expressed and are operable in the host organism.

DNA regions are operably linked or operably associated when they are functionally related to each other. For example, a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Transformed host cells are cells which have been transformed or transfected with vectors containing DNA coding for lantibiotics of the present invention need not express protein.

Suitable host cells include prokaryotes, yeast cells, or higher eukaryotic organism cells. Prokaryote host cells include gram negative or gram positive organisms, for example *Escherichia coli* (*E. coli*) or *Bacilli*. Higher eukaryotic cells include established cell lines of mammalian origin as described below. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. See Bolivar et al., *Gene* 2, 95 (1977). Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983). The promoter and Shine-Dalgarno sequence (for prokaryotic host expression) are operably linked to the DNA of the present invention, i.e., they are positioned so as to promote transcription of the messenger RNA from the DNA.

Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983). While these are commonly used, other microbial promoters are suitable. Details concerning nucleotide sequences of many have been published, enabling a skilled worker to operably ligate them to DNA encoding the protein in plasmid or viral vectors (Siebenlist et al., *Cell* 20, 269 (1980). The promoter and Shine-Dalgarno sequence (for prokaryotic host expression) are operably linked to the DNA encoding the desired protein, i.e., they are positioned so as to promote transcription of the protein messenger RNA from the DNA.

Eukaryotic microbes such as yeast cultures may be transformed with suitable protein-encoding vectors. See e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or anautonomously replicating sequence (ARS), a promoter, DNA encoding the desired protein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980). This plasmid contains the trp1 gene, which provides a selection marker for a mutant strain of yeast lacking the ability to grow in tryptophan, for example ATCC No. 44076 or PEP4-1 (Jones, *Genetics* 85, 12 (1977). The presence of the trp1 lesion in the yeast host cell genome then provides an effective environment for detecting transformation by growth in the absence of tryptophan.

Suitable promoting sequences in yeast vectors include the promoters for metallothionein, 3-phospho-glycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Preduramycin, produramycin or duramycin may be produced in recombinant host cells produced as described above by culturing the cells under conditions which cause or permit the expression and production of the desired protein, all in accordance with known techniques.

Preduramycin and produramycin as described herein are useful as intermediates for the production of duramycin, either by transformation and processing in situ in a host cell, or by subsequent chemical/synthetic modification.

Duramycin produced by the methods described herein is useful as an antibiotic or for treating disorders such as cystic fibrosis, chronic bronchitis, and asthma, including but not limited to those uses described in U.S. Pat. No. 5,849,706 to Molina and U.S. Pat. No. 6,451,365 to King, the disclosures of which are incorporated by reference herein in their entirety.

The examples, which follow, are set forth to illustrate the present invention, and are not to be construed as limiting thereof.

EXAMPLE 1

Isolation of the Duramycin Structural Gene

The duramycin-producing strain *Streptomyces cinnamoneus* subsp. *cinnamoneus* (ATCC 12686) was grown in yeast extract malt extract (YEME), 10% sucrose, 0.5% glycine. Genomic DNA was isolated using the well-known cetyltrimethylammonium bromide (CTAB) method (Keiser, et al. (2000) In: Practical *Streptomyces* Genetics). The propeptide amino acid sequence of duramycin (SEQ ID NO:5) is similar to other Type-B lantibiotics produced by *Streptomyces* such as cinnamycin (SEQ ID NO:8), duramycin B (SEQ ID NO:9), duramycin C (SEQ ID NO:10), and ancovenin (SEQ ID NO:11) (FIG. 2). Polymerase chain reaction (PCR) primers (Table 1) were designed based on the nucleotide sequence encoding precinnamycin (GENBANK® Accession No. X58545; SEQ ID NO:12; FIG. 3).

TABLE 1

| PRIMER POSITION | PRIMER NAME | SEQUENCE | SEQ ID NO: |
|---|---|---|---|
| Forward | Mol1 | 5'-CCTCAACATCGGAGGTAAG-3' | SEQ ID NO: 14 |
| Reverse | Mol2 | 5'-GCATTACCGCCTAGAGGCA-3' | SEQ ID NO: 15 |
| Forward | Mol3 | 5'-AACATCGGAGGTAAGCCATG-3' | SEQ ID NO: 16 |
| Reverse | Mol4 | 5'-AGGCAGCAGCCACTTACTT-3' | SEQ ID NO: 17 |
| Forward | Mol5 | 5'-TTCAGCAGTCCGTCGTGGA-3' | SEQ ID NO: 18 |
| Reverse | Mol6 | 5'-TTGCCGTCGCACACGAAGGT-3' | SEQ ID NO: 19 |

All nine combinations of forward and reverse primers were used in PCR reactions with *S. cinnamoneus* ATCC12686 genomic DNA as a template. All three forward primers when used in combination with reverse primer Mol6 consistently amplified a PCR product of the expected size. Two independent amplicons were directly sequenced and found to contain the duramycin structural gene. An amplicon from the Mol1/Mol6-primed PCR reaction was subcloned using the TA CLONING® kit (INVITROGEN™. Carlsbad, Calif.) and subsequently used to generate a hybridization probe with the ALK-PHOS DIRECTS™ labeling kit (AMERSHAM™, Piscataway, N.J.). Southern blot analysis of *S. cinnamoneus* ATCC12686 genomic DNA detected a single durA band in each of several restriction enzyme digests, including BamHI, KpnI and XhoI. This same probe was used for subsequent screening of a genomic library.

A cosmid library, constructed from DNA isolated from strain ATCC 12686, was screened using the duramycin probe to identify large (>30 kilobase) stretches of flanking DNA to isolate the lantibiotic biosynthetic operon. High molecular weight genomic DNA was isolated using the CTAB method above. Subsequently, the DNA was partially digested with Sau3A restriction enzyme using well-known methods to yield a pool of fragments with an average size of ~40-kb (In: Current Protocols in Molecular Biology, Ausubel, et al. (eds), John Wiley & Sons). The cosmid library was constructed using the SuperCos Cosmid Library Kit (STRATAGENE®, La Jolla, Calif.). The library contained ~15,000 clones. Ten, randomly selected clones were analyzed by restriction enzyme digestion; all clones contained inserts of at least 30-kb. Four thousand clones were screened by colony hybridization on nitrocellulose filters using the non-radioactive durA probe previously described. Four positive clones were isolated. The presence of the duramycin structural gene in the cosmid clones was verified by amplifying and directly sequencing amplicons generated with durA-specific primers and cosmid clone DNA as a template. Two overlapping cosmid clones, 1.1 and 3.4, were selected for shotgun sequencing.

The TOPO® Shotgun Cloning Kit (INVITROGEN™, Carlsbad, Calif.) was used for shearing the cosmid DNA by nebulization to generate random fragments of ~1-kb. The ends of the sheared DNA were made blunt by T4 DNA polymerase and Klenow and subsequently ligated into pCR®4Blunt-TOPO® vector (INVITROGEN™, Carlsbad, Calif.). More than 300 subclones for each cosmid were obtained and 288 clones for each cosmid were picked into three, 96-deep-well plates. Two, 96-well plates for each cosmid were used to prepare template DNA with the EPPENDORF® 96-well plasmid prep kit (EPPENDORF® AG, Hamburg, Germany). Templates were used for high-throughput sequencing using an ABI PRISMS® 3700 DNA Analyzer (APPLIED BIOSYSTEMS®, Foster City, Calif.) with universal forward and reverse sequencing primers.

A contiguous DNA sequence of ~46-kb was obtained. This represented 17-kb of overlap between the two cosmids with an additional 23-kb of 1.1 flanking DNA and 6-kb of 3.4 flanking DNA. In addition to the structural gene encoding duramycin, sequences homologous to the durM, durF, and durR genes of the duramycin biosynthetic operon were contained within these two cosmids.

Deduced amino acid sequence analysis revealed that preduramycin contains a 58 amino acid leader sequence (SEQ ID NO:7) and a 19 amino acid propeptide (SEQ ID NO:5) which is post-translationally modified to generate the mature lantibiotic. The deduced amino acid sequence of preduramycin (SEQ ID NO:3) shares a high degree of homology with that of cinnamycin (SEQ ID NO:13) (FIG. 4).

The foregoing examples are illustrative of the present invention, and are not to be construed as limiting thereof. The invention is described by the following claims, with equivalents of the claims to be included therein.

That which is claimed is:

1. An isolated nucleic acid selected from the group consisting of:
   (a) nucleic acid according to SEQ ID NO: 2 encoding preduramycin;
   (b) a nucleic acid according to SEQ ID NO: 4 encoding produramycin;
   (c) nucleic acids that are at least 95 percent identical in sequence to nucleic acids of (a) or (b) above and which encode said preduramycin or produramycin;
   (d) nucleic acids that differ from the nucleic acids of (a), (b), or (c) above due to the degeneracy of the genetic code, and which encode a preduramycin encoded by a nucleic acid of (a),(b), or (c) above, and
   wherein the preduramycin and produramycin are precursors of duramycin, which is an antibiotic.

2. The nucleic acid according to claim 1, wherein said nucleic acid is a DNA.

3. The nucleic acid according to claim 1 having a sequence according to SEQ ID NO: 2.

4. The nucleic acid according to claim 1 having a sequence according to SEQ ID NO: 4.

5. A recombinant nucleic acid comprising a nucleic acid according to claim 1 operatively associated with a promoter.

6. A vector comprising a recombinant nucleic acid according to claim 5.

7. The vector of claim 6, wherein said vector is a plasmid.

8. An isolated recombinant host cell comprising a heterologous nucleic acid according to claim 1 and capable of expressing the encoded preduramycin or produramycin.

9. The recombinant host cell of claim 8, wherein said cell is gram positive bacteria.

10. The recombinant host cell of claim 8, wherein said cell is selected from the group consisting of genus *Bacillus*, genus *Streptomyces*, and genus *Streptococcus*.

11. A method of making preduramycin, produramycin, or duramycin, comprising:
    cultering a suitable host cell according to claim 8 under conditions which the encoded preduramycin or produramycin is expressed; and then
    collecting preduramycin, produramycin or duramycin from said cultered host cells.

12. The method of claim 11, wherein said host cell is a gram positive bacteria.

13. The method of claim 11, wherein said host cell is selected from the group consisting of genus *Bacillus*, genus *Streptomyces* and genus *Streptococcus*.

14. The method of claim 11, wherein said culturing step is carried out under conditions in which duramycin is produced by said host cell; and wherein said collecting step comprises collecting duramycin from said cultured host cells.

* * * * *

SEQUENCE LISTING

```
<160> NUMBER OF SEQ ID NOS: 19

<210> SEQ ID NO 1
<211> LENGTH: 271
<212> TYPE: DNA
<213> ORGANISM: Streptomyces cinnamoneus

<400> SEQUENCE: 1
cctcaacatc ggaggtaagt catgaccgct tcgattcttc agtccgtcgt ggacgccgac      60
ttccgcgccg cgctgatcga gaacccggcc gcgttcggtg cctcgaccgc ggtcctgccc     120
```

```
acgcccgtgg agcagcagga ccaggcgtcc ctcgacttct ggaccaagga catcgccgct      180
acggaagcct tcgcctgcaa gcagagctgc agcttcggcc cgttcacctt cgtgtgtgac      240
ggcaacacca agtaaggcgg ccgttgccct c                                     271

<210> SEQ ID NO 2
<211> LENGTH: 231
<212> TYPE: DNA
<213> ORGANISM: Streptomyces cinnamoneus

<400> SEQUENCE: 2
atgaccgctt cgattcttca gtccgtcgtg gacgccgact ccgcgccgc gctgatcgag       60 aacccggccg cgttcggtgc ctcgaccgcg gtcctgccca cgcccgtgga gcagcaggac      120
caggcgtccc tcgacttctg gaccaaggac atcgccgcta cggaagcctt cgcctgcaag      180
cagagctgca gcttcggccc gttcaccttc gtgtgtgacg gcaacaccaa g               231

<210> SEQ ID NO 3
<211> LENGTH: 77
<212> TYPE: PRT
<213> ORGANISM: Streptomyces cinnamoneus

<400> SEQUENCE: 3

Met Thr Ala Ser Ile Leu Gln Ser Val Val Asp Ala Asp Phe Arg Ala
1               5                   10                  15

Ala Leu Ile Glu Asn Pro Ala Ala Phe Gly Ala Ser Thr Ala Val Leu
            20                  25                  30

Pro Thr Pro Val Glu Gln Gln Asp Gln Ala Ser Leu Asp Phe Trp Thr
        35                  40                  45

Lys Asp Ile Ala Ala Thr Glu Ala Phe Ala Cys Lys Gln Ser Cys Ser
    50                  55                  60

Phe Gly Pro Phe Thr Phe Val Cys Asp Gly Asn Thr Lys
65                  70                  75

<210> SEQ ID NO 4
<211> LENGTH: 57
<212> TYPE: DNA
<213> ORGANISM: Streptomyces cinnamoneus

<400> SEQUENCE: 4
tgcaagcaga gctgcagctt cggcccgttc accttcgtgt gtgacggcaa caccaag         57

<210> SEQ ID NO 5
<211> LENGTH: 19
<212> TYPE: PRT
<213> ORGANISM: Streptomyces cinnamoneus

<400> SEQUENCE: 5

Cys Lys Gln Ser Cys Ser Phe Gly Pro Phe Thr Phe Val Cys Asp Gly
1               5                   10                  15

Asn Thr Lys

<210> SEQ ID NO 6
<211> LENGTH: 174
<212> TYPE: DNA
<213> ORGANISM: Streptomyces cinnamoneus

<400> SEQUENCE: 6
atgaccgctt cgattcttca gtccgtcgtg gacgccgact ccgcgccgc gctgatcgag       60
```

```
aacccggccg cgttcggtgc ctcgaccgcg gtcctgccca cgcccgtgga gcagcaggac    120
caggcgtccc tcgacttctg gaccaaggac atcgccgcta cggaagcctt cgcc         174
```

<210> SEQ ID NO 7
<211> LENGTH: 58
<212> TYPE: PRT
<213> ORGANISM: Streptomyces cinnamoneus

<400> SEQUENCE: 7

```
Met Thr Ala Ser Ile Leu Gln Ser Val Val Asp Ala Asp Phe Arg Ala
1               5                   10                  15

Ala Leu Ile Glu Asn Pro Ala Ala Phe Gly Ala Ser Thr Ala Val Leu
            20                  25                  30

Pro Thr Pro Val Glu Gln Gln Asp Gln Ala Ser Leu Asp Phe Trp Thr
        35                  40                  45

Lys Asp Ile Ala Ala Thr Glu Ala Phe Ala
    50                  55
```

<210> SEQ ID NO 8
<211> LENGTH: 19
<212> TYPE: PRT
<213> ORGANISM: Streptomyces griseoverticillatus

<400> SEQUENCE: 8

```
Cys Arg Gln Ser Cys Ser Phe Gly Pro Phe Thr Phe Val Cys Asp Gly
1               5                   10                  15

Asn Thr Lys
```

<210> SEQ ID NO 9
<211> LENGTH: 19
<212> TYPE: PRT
<213> ORGANISM: Streptomyces sp,

<400> SEQUENCE: 9

```
Cys Arg Gln Ser Cys Ser Phe Gly Pro Leu Thr Phe Val Cys Asp Gly
1               5                   10                  15

Asn Thr Lys
```

<210> SEQ ID NO 10
<211> LENGTH: 19
<212> TYPE: PRT
<213> ORGANISM: Streptomyces sp.

<400> SEQUENCE: 10

```
Cys Ala Asn Ser Cys Ser Tyr Gly Pro Leu Thr Trp Ser Cys Asp Gly
1               5                   10                  15

Asn Thr Lys
```

<210> SEQ ID NO 11
<211> LENGTH: 19
<212> TYPE: PRT
<213> ORGANISM: Streptomyces sp.

<400> SEQUENCE: 11

```
Cys Val Gln Ser Cys Ser Phe Gly Pro Leu Thr Trp Ser Cys Asp Gly
1               5                   10                  15

Asn Thr Lys
```

<210> SEQ ID NO 12
<211> LENGTH: 285

-continued

```
<212> TYPE: DNA
<213> ORGANISM: Streptomyces griseoverticillatus

<400> SEQUENCE: 12
cctcaacatc ggaggtaagc catgaccgct tccattcttc agcagtccgt cgtggacgcc      60
gacttccgcg cggcgctgct tgagaacccc gccgccttcg gcgcttccgc cgcggccctg     120
cccacgcccg tcgaggccca ggaccaggcg tcccttgact tctggaccaa ggacatcgcc     180
gccacggaag ccttcgcctg ccgccagagc tgcagcttcg gcccgttcac cttcgtgtgc     240
gacggcaaca ccaagtaagt ggctgctgcc tctaggcggt aatgc                     285

<210> SEQ ID NO 13
<211> LENGTH: 78
<212> TYPE: PRT
<213> ORGANISM: Streptomyces griseoverticillatus

<400> SEQUENCE: 13

Met Thr Ala Ser Ile Leu Gln Gln Ser Val Val Asp Ala Asp Phe Arg
1               5                   10                  15

Ala Ala Leu Leu Glu Asn Pro Ala Ala Phe Gly Ala Ser Ala Ala Ala
            20                  25                  30

Leu Pro Thr Pro Val Glu Ala Gln Asp Gln Ala Ser Leu Asp Phe Trp
        35                  40                  45

Thr Lys Asp Ile Ala Ala Thr Glu Ala Phe Ala Cys Arg Gln Ser Cys
    50                  55                  60

Ser Phe Gly Pro Phe Thr Phe Val Cys Asp Gly Asn Thr Lys
65                  70                  75

<210> SEQ ID NO 14
<211> LENGTH: 19
<212> TYPE: DNA
<213> ORGANISM: Artificial Sequence
<220> FEATURE:
<223> OTHER INFORMATION: Synthetic primer

<400> SEQUENCE: 14
cctcaacatc ggaggtaag                                                   19

<210> SEQ ID NO 15
<211> LENGTH: 19
<212> TYPE: DNA
<213> ORGANISM: Artificial Sequence
<220> FEATURE:
<223> OTHER INFORMATION: Synthetic primer

<400> SEQUENCE: 15
gcattaccgc ctagaggca                                                   19

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
aacatcggag gtaagccatg                                                  20

<210> SEQ ID NO 17
<211> LENGTH: 19
<212> TYPE: DNA
<213> ORGANISM: Artificial Sequence
```

```
<220> FEATURE:
<223> OTHER INFORMATION: Synthetic primer

<400> SEQUENCE: 17
aggcagcagc cacttactt                                                  19

<210> SEQ ID NO 18
<211> LENGTH: 19
<212> TYPE: DNA
<213> ORGANISM: Artificial Sequence
<220> FEATURE:
<223> OTHER INFORMATION: Synthetic primer

<400> SEQUENCE: 18
ttcagcagtc cgtcgtgga                                                  19

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
ttgccgtcgc acacgaaggt                                                 20
```